United States Patent
Mitsuyoshi

(10) Patent No.: US 10,325,616 B2
(45) Date of Patent: Jun. 18, 2019

(54) INTENTION EMERGENCE DEVICE, INTENTION EMERGENCE METHOD, AND INTENTION EMERGENCE PROGRAM

(71) Applicants: JAPAN MATHEMATICAL INSTITUTE INC., Tokyo (JP); Shunji Mitsuyoshi, Tokyo (JP)

(72) Inventor: Shunji Mitsuyoshi, Tokyo (JP)

(73) Assignee: JAPAN MATHEMATICAL INSTITUTE INC., Tokyo (JP)

( * ) Notice: Subject to any disclaimer, the term of this patent is extended or adjusted under 35 U.S.C. 154(b) by 0 days.

(21) Appl. No.: 16/083,324

(22) PCT Filed: Mar. 27, 2017

(86) PCT No.: PCT/JP2017/012398
§ 371 (c)(1),
(2) Date: Sep. 7, 2018

(87) PCT Pub. No.: WO2017/170404
PCT Pub. Date: Oct. 5, 2017

(65) Prior Publication Data
US 2019/0027163 A1    Jan. 24, 2019

(30) Foreign Application Priority Data

Mar. 30, 2016  (JP) .................. 2016-068827
Mar. 21, 2017  (JP) .................. 2017-054238

(51) Int. Cl.
*G10L 25/63*    (2013.01)
*G06F 3/01*    (2006.01)
(Continued)

(52) U.S. Cl.
CPC ............. *G10L 25/63* (2013.01); *A61B 5/16* (2013.01); *G06F 3/011* (2013.01); *G06F 3/16* (2013.01);
(Continued)

(58) Field of Classification Search
CPC . G10L 25/63; G06F 3/16; G06F 3/011; G06F 2203/011; A61B 5/16; A61B 5/01;
(Continued)

(56) References Cited

U.S. PATENT DOCUMENTS 5,367,454 A  * 11/1994  Kawamoto ............ G06N 3/004
                                                       345/418
2012/0083700 A1 *  4/2012  Osorio ................. A61B 5/0245
                                                       600/483
(Continued)

FOREIGN PATENT DOCUMENTS

JP       H06-12401 A       1/1994
JP       2009-294647 A    12/2009
(Continued)

OTHER PUBLICATIONS

Jun. 20, 2017 International Search Report issued in International Patent Application No. PCT/JP2017/012398.

*Primary Examiner* — Edwin S Leland, III
(74) *Attorney, Agent, or Firm* — Oliff PLC

(57) ABSTRACT

An acquisition unit acquiring data including sound information uttered by a subject; a detection unit detecting feelings of the subject using the acquired data; a decision unit deciding weighting coefficients for data in accordance with the feelings of the subject; a calculation unit calculating energy which involves in human emotions and organ activities; a plurality of elements outputting signals each of which indicates the change in a state of the element as homeostasis in each of the human emotions and the organ activities; an emergence unit deciding feelings and intentions in accordance with the signals output from the elements; and a control unit performing phase transition of the state of the elements when an amount of change in the state of at least one element is equal to or less than a predetermined amount
(Continued)

or when the state of at least one element is in a predetermined state.

5 Claims, 5 Drawing Sheets

(51) Int. Cl.
*G06F 3/16* (2006.01)
*A61B 5/16* (2006.01)
*G06N 3/00* (2006.01)
*A61B 5/00* (2006.01)
*A61B 7/00* (2006.01)
*A61B 5/01* (2006.01)
*A61B 5/0205* (2006.01)
*A61B 5/021* (2006.01)
*A61B 5/0245* (2006.01)
*A61B 5/0476* (2006.01)
*A61B 5/053* (2006.01)
*A61B 5/055* (2006.01)
*A61B 5/1468* (2006.01)

(52) U.S. Cl.
CPC ............... *G06N 3/00* (2013.01); *A61B 5/01* (2013.01); *A61B 5/021* (2013.01); *A61B 5/0205* (2013.01); *A61B 5/0245* (2013.01); *A61B 5/0476* (2013.01); *A61B 5/055* (2013.01); *A61B 5/0533* (2013.01); *A61B 5/1468* (2013.01); *A61B 5/163* (2017.08); *A61B 5/7264* (2013.01); *A61B 7/003* (2013.01); *G06F 2203/011* (2013.01)

(58) Field of Classification Search
CPC ....... A61B 5/021; A61B 5/0205; A61B 5/163; A61B 7/003; A61B 5/7264; A61B 5/055; A61B 5/0533; A61B 5/0476; A61B 5/0245; A61B 5/1468; G06N 3/00
USPC ........................................................ 704/270
See application file for complete search history.

(56) References Cited

U.S. PATENT DOCUMENTS

| 2012/0116186 | A1* | 5/2012 | Shrivastav | A61B 5/0507 600/301 |
| 2017/0000397 | A1* | 1/2017 | Mitsuyoshi | A61B 5/72 |
| 2017/0245759 | A1* | 8/2017 | Jain | A61B 5/0002 |
| 2017/0249438 | A1* | 8/2017 | Jain | G10L 25/63 |
| 2017/0337438 | A1* | 11/2017 | el Kaliouby, Jr. | A61B 5/0077 |
| 2018/0206725 | A1* | 7/2018 | Everett | A61B 5/1116 |
| 2019/0027163 | A1* | 1/2019 | Mitsuyoshi | A61B 5/16 |

FOREIGN PATENT DOCUMENTS

| JP | 2009294647 A | * 12/2009 |
| JP | 2015-128579 A | 7/2015 |
| JP | 2016-12341 A | 1/2016 |

* cited by examiner

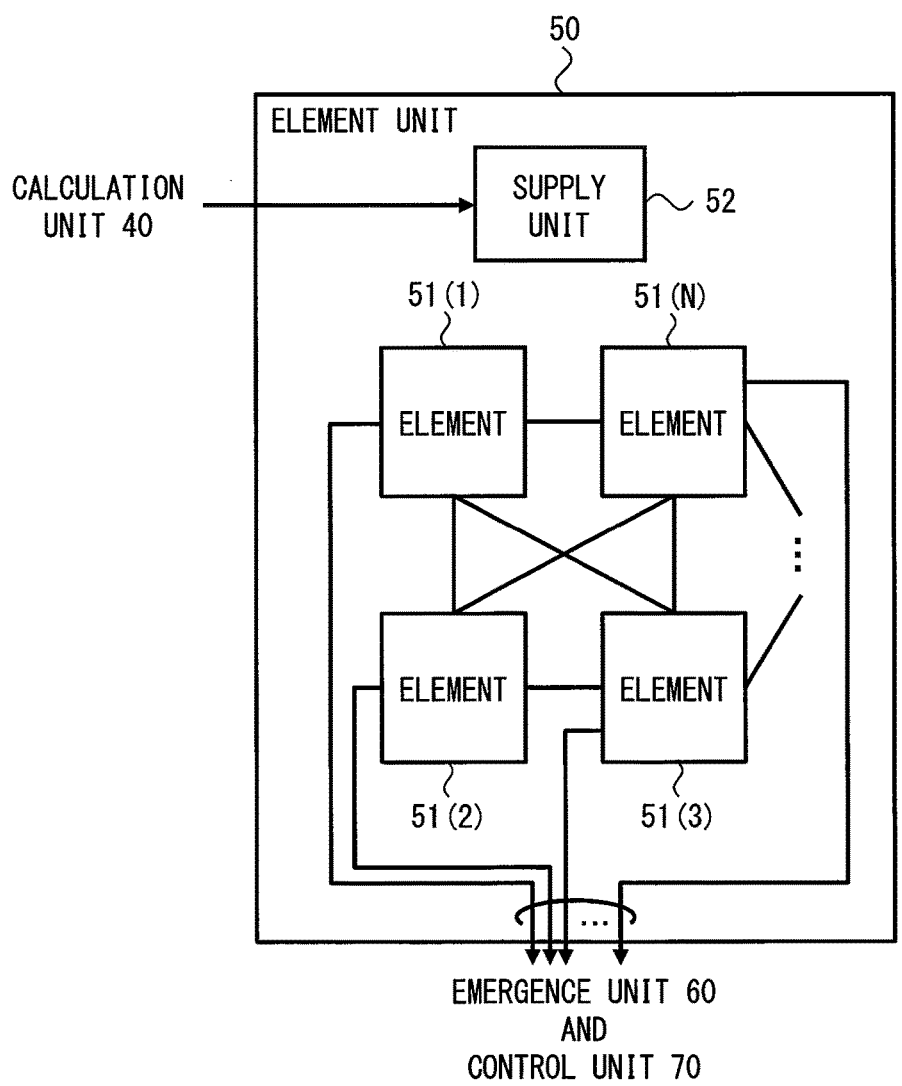

FIG. 4

| FEELINGS AND INTENTIONS | ELEMENT51 (1) | ELEMENT51 (2) | ELEMENT51 (3) | ... | ELEMENT51 (N) |
|---|---|---|---|---|---|
| ANGER, SUPPRESS | CHANGE STATE a1 TO STATE a2 | CHANGE IN RANGE OF STATE b1 TO b2 | FIXED IN STATE c1 | ... | CHANGE STATE n1 TO STATE n2 |
| ANGER, RETORT | CHANGE STATE a1 TO STATE a2 | CHANGE IN RANGE OF STATE b1 TO b2 | — | ... | FIXED IN STATE n3 |
| ... | ... | ... | ... | ... | ... |
| NORMAL, CONVERSE | FIXED IN STATE a3 | CHANGE IN RANGE OF STATE b3 TO b4 | CHANGE IN RANGE OF STATE c2 TO c3 | ... | — |
| NORMAL, AGREE | FIXED IN STATE a3 | CHANGE IN RANGE OF STATE b3 TO b4 | CHANGE IN RANGE OF STATE c4 TO c5 | ... | — |
| ... | ... | ... | ... | ... | ... |

ET

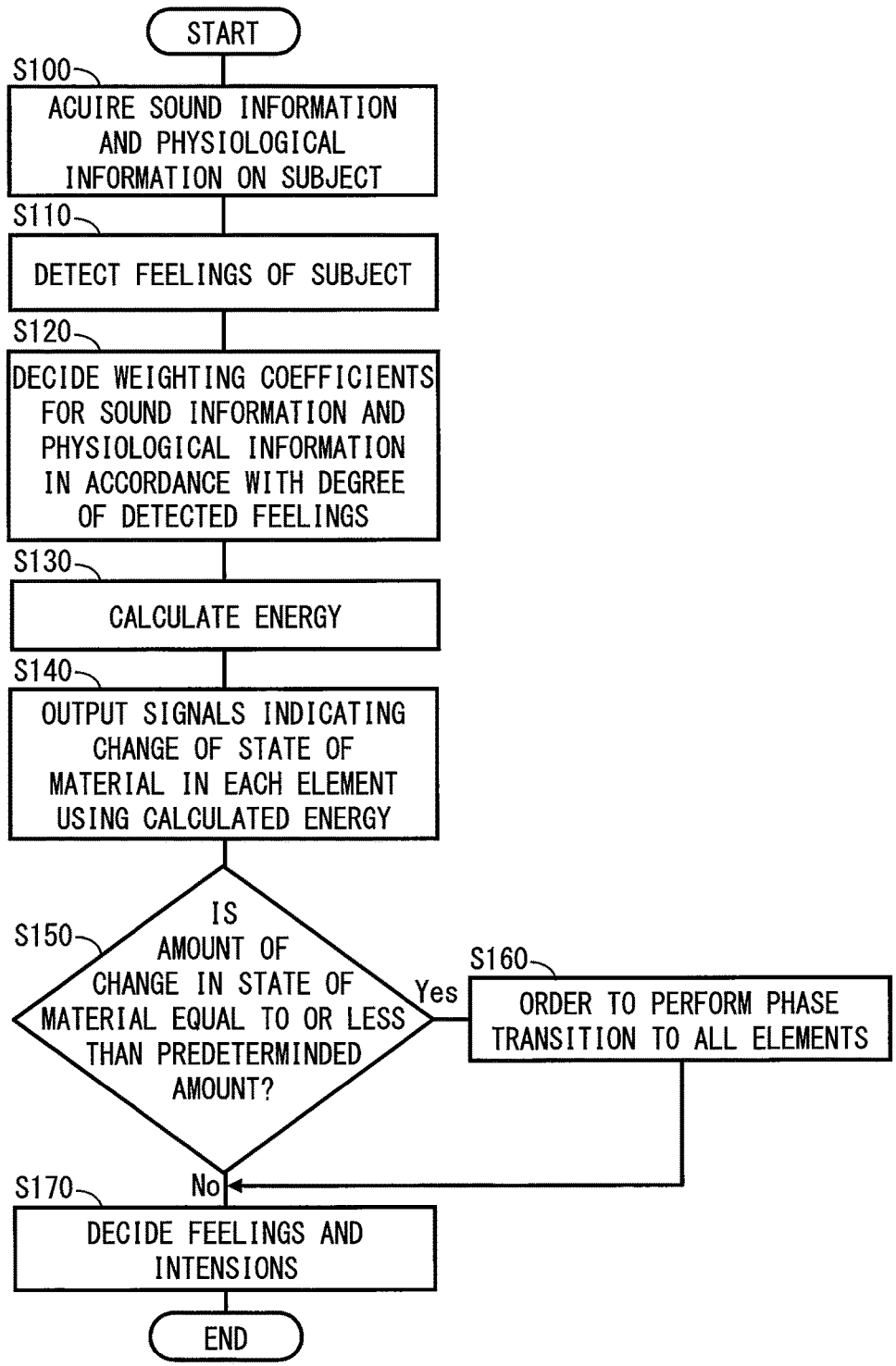

INTENTION EMERGENCE DEVICE, INTENTION EMERGENCE METHOD, AND INTENTION EMERGENCE PROGRAM

CROSS REFERENCE TO RELATED APPLICATION

This application is a U.S. National Stage application claiming the benefit of prior filed International Application Number PCT/JP2017/012398, filed on Mar. 27, 2017, in which the International Application claims priority from Japanese Patent Application Number 2016-068827 and Japanese Patent Application Number 2017-054238, filed on Mar. 30, 2016 and Mar. 21, 2017, respectively, the entire contents of which are incorporated herein by reference.

TECHNICAL FIELD

The present invention relates to an intention emergence device, an intention emergence method, and an intention emergence program.

BACKGROUND ART

Attempts have been made to reproduce reactions such as a double-loop and a triple-loop which occurs in a human brain determination process, using techniques of the related art such as a Von Neumann computer, artificial intelligence, a neural network, and deep learning.

On the other hand, techniques for estimating the state of a human, such as emotion or physiology, without using a calculation method (that is, binary system) using a huge number of switches have been proposed. For example, in Patent Document 1, a deviation amount of homeostasis in a test subject is obtained using information indicating the physiological state of the test subject and information indicating emotions and organ activities, such as the brain, of the test subject, and energy which involves in emotions and organ activities of the test subject is calculated from the obtained deviation amount. In Patent Document 1, a technique is proposed in which a plurality of gears indicating the emotions and each of the organ activities of the test subject are rotated in a virtual space using the calculated energy to estimate the pathology of the test subject from the state of rotation of each gear.

PRIOR ART DOCUMENT

Patent Document

Patent Document 1: Japanese Unexamined Patent Application Publication No. 2015-128579

DISCLOSURE

Problems to be Solved

However, in a method using a Von Neumann computer of the related art, or the like, it is possible to cope with only the probability and differentiation in calculation means using a binary system, and thus the calculation is repeated infinitely. For this reason, in a method using a Von Neumann computer or the like, it is difficult to maintain a calculation amount within a range of the storage capacity of a memory or the like without diverging calculations (a reaction such as a double-loop) to be repeatedly executed, as in a human brain determination process. That is, in the method using a Von Neumann computer or the like, it is difficult to reproduce a reaction such as a double-loop in the human brain determination process and to decide a timing for deciding intention, determination, and the like (a timing for converging a reaction (calculation to be repeatedly executed) such as a double-loop). In addition, in the method using a Von Neumann computer or the like, it is difficult to decide various intentions, determinations, and the like according to one's own mood, conditions, scenes, and the like. These are known as frame problems of artificial intelligence.

In an aspect, an intention emergence device, an intention emergence method, and an intention emergence program of the present disclosure are intended to be capable of making emergence various intentions.

Means for Solving the Problems

An intention emergence device according to an aspect includes an acquisition unit acquiring data including at least sound information uttered by a subject; a detection unit detecting feelings of the subject using the acquired data; a decision unit deciding weighting coefficients for the data acquired in accordance with the detected feelings of the subject; a calculation unit calculating energy which involves in human emotions and organ activities with the data and the coefficients; a plurality of elements, each of which has a material changing a state in accordance with input of the energy calculated by the calculation unit, outputting signals each of which indicates the change in the state of the material as homeostasis in each of the human emotions and the organ activities; an emergence unit deciding feelings and intentions in accordance with the change in the state of the material included in the signals output from each of the plurality of elements; and a control unit performing phase transition of the state of the material in each of the plurality of elements when an amount of change in the state of the material in at least one element among the plurality of elements is equal to or less than a predetermined amount or when the state of the material in at least one element among the plurality of elements is in a predetermined state.

An intention emergence method according to another aspect includes acquiring data including at least sound information uttered by a subject; detecting feelings of the subject using the acquired data; deciding weighting coefficients for the data acquired in accordance with the detected feelings; calculating energy which involves in human emotions and organ activities with the data and the coefficients: inputting the calculated energy to each of a plurality of elements which has a material changing a state in accordance with the input, and outputting, from each of the plurality of elements, signals each of which indicates the change in the state of the material as homeostasis in each of the human emotions and the organ activities; deciding feelings and intentions in accordance with the change in the state of the material included in the signals output from each of the plurality of elements; and performing phase transition of the state of the material in each of the plurality of elements when an amount of change in the state of the material in at least one element among the plurality of elements is equal to or less than a predetermined amount or when the state of the material in at least one element among the plurality of elements is in a predetermined state.

An intention emergence program according to still another aspect causes a computer to execute a process including acquiring data including at least sound information uttered by a subject; detecting feelings of the subject using the acquired data; deciding weighting coefficients for the data acquired in accordance with the detected feelings; calculating energy which involves in human emotions and organ activities with the data and the coefficients; inputting the calculated energy to each of a plurality of elements which has a material changing a state in accordance with the input, and outputting, from each of the plurality of elements, signals each of which indicates the change in the state of the material as homeostasis in each of the human emotions and the organ activities; deciding feelings and intentions in accordance with the change in the state of the material included in the signals output from each of the plurality of elements; and performing phase transition of the state of the material in each of the plurality of elements when an amount of change in the state of the material in at least one element among the plurality of elements is equal to or less than a predetermined amount or when the state of the material in at least one element among the plurality of elements is in a predetermined state.

An intention emergence device, an intention emergence method, and an intention emergence program of the present disclosure are capable of making emergence various intentions.

BRIEF DESCRIPTION OF DRAWINGS

FIG. 3 is a diagram illustrating an example of an element unit illustrated in FIG. 1.

FIG. 4 is a diagram illustrating an example of an emergence table illustrated in FIG. 1.

FIG. 5 is a diagram illustrating an example of an intention emergence process in the intention emergence device illustrated in FIG. 1.

DETAILED DESCRIPTION OF THE EMBODIMENTS

Hereinafter, an embodiment will be described with reference to the accompanying drawings.

Figure 1:
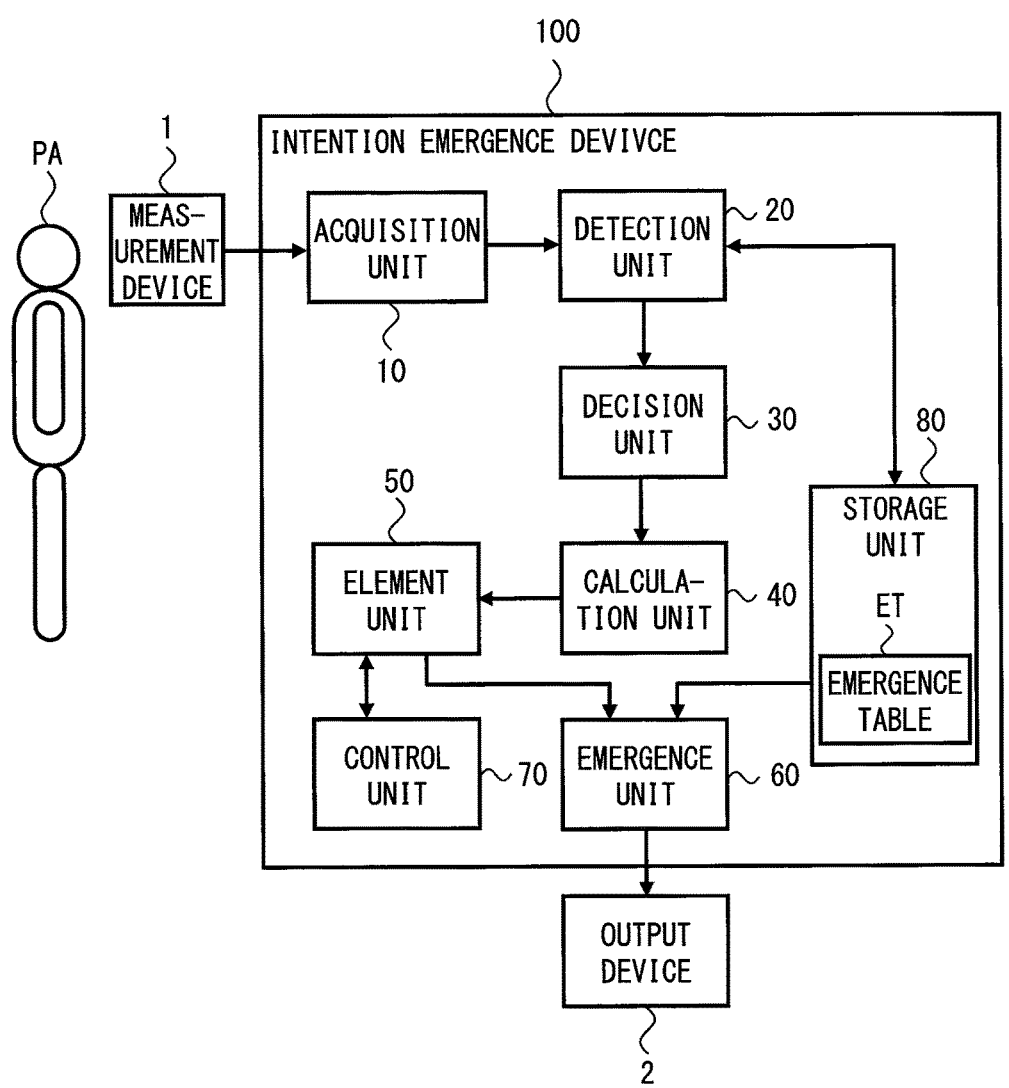
FIG. 1 is a diagram illustrating an intention emergence device according to an embodiment.

FIG. 1 illustrates an intention emergence device according to an embodiment.

An intention emergence device 100 illustrated in FIG. 1 is a computer device including an execution processing device such as a central processing unit (CPU) and a storage unit 80 such as a hard disk drive, or the like. The intention emergence device 100 is connected to a measurement device 1 and an output device 2 in a wired or wireless manner through an input-output interface included in the intention emergence device 100, or the like.

The measurement device includes, for example, at least a microphone, and measures a sound signal uttered by a subject PA to be detected, as sound information. The measurement device 1 outputs data including the measured sound information on the subject PA to the intention emergence device 100. Meanwhile, the measurement device 1 includes a plurality of apparatuses such as a heart rate meter, an electrocardiograph, a sphygmomanometer, a clinical thermometer, a skin resistance meter, a camera, and a magnetic resonance imaging (MRI) device, and also measures physiological information such as the blood pressure and body temperature of the subject PA. The measurement device 1 outputs data including the measured physiological information on the subject PA and the sound information to the intention emergence device 100. In addition, the measurement device 1 may include an acceleration sensor, an electronic gyroscope, or the like.

Meanwhile, the physiological information on the subject PA which is measured by the measurement device 1 includes, for example, a heart (pulse) rate, a heart rate fluctuation, blood pressure, body temperature, the amount of perspiration (skin resistance, skin potential), the motion of an eyeball, a pupil diameter, and the number of times of winking. In addition, the measured physiological information includes, for example, sighs, hormone, and secretions in the body such as biomolecules, brain waves, functional MRI (fMRI) information, and the like.

For example, the heart (pulse) rate is measured using the heart rate meter included in the measurement device 1, or the like, and there is a property that a heart rate increases by an increase in the amount of adrenalin secreted in the body due to excitement or tension.

For example, the heart rate fluctuation is acquired by executing spectrum analysis such as fast Fourier transform (FFT) on an electrocardiographic waveform of the subject PA which is measured using an electrocardiograph included in the measurement device 1. It is possible to acquire the level of excitement or tension of the subject PA by comparing the amount of low frequency components LF (for example, 0.04 hertz to 0.14 hertz) with the amount of high frequency components HF (for example, 0.14 hertz to 0.5 hertz) of the heart rate fluctuation. Meanwhile, there is a property that the low frequency components LF of the heart rate fluctuation increase mainly in association with the activity of sympathetic nerves and the high frequency components HF increase in association with the activity of parasympathetic nerves.

For example, the blood pressure is measured using the sphygmomanometer included in the measurement device 1, and there is a property that the blood pressure rises by contraction of a blood vessel of the subject PA and an increase in resistance to bloodstream in association with excitement or tension.

For example, the body temperature is measured using the clinical thermometer included in the measurement device 1, or the like, and there is a property that heat is generated in the body due to an increase in a heart rate, an increase in a blood sugar level, the occurrence of muscular tension, and the like in association with excitement or tension, which leads to an increase in body temperature.

For example, the amount of perspiration (skin resistance, skin potential) is measured using the skin resistance meter included in the measurement device 1, or the like, and there is a property that perspiration is promoted due to excitement or tension, which leads to a decrease in skin resistance.

For example, the motion of an eyeball, a pupil diameter, and the number of times of winking are measured using an eye electrometer or the camera of the measurement device 1, or the like. There is a property that the motion of an eyeball becomes intense due to excitement or tension, the pupil diameter is increased due to excitement or tension, and the number of times of winking is increased due to excitement or tension.

For example, the sighs are measured as the number of sighs, speed, displacement, and the like from the amount of breathing and a breathing sound using a breathing meter (breathing flow meter) included in the measurement device 1, a spirometer, a microphone, or the like, and there is a property that the number of sighs, speed, and displacement are increased due to excitement or tension.

For example, the secretions in the body such as hormone and biomolecules are measured using the analysis device included in the measurement device 1 by performing chemical analysis of saliva, blood, lymph, sweat, digestive juices, urine, or the like which is taken from the subject PA. In addition, the secretions in the body may be measured by the measurement device 1 from a peripheral vessel, digestive system, muscle potential, skin temperature, blood flow rate, immune system, or the like of the subject PA. In addition, with regard to the secretions in the body, there is a property that the amount or quality of hormone or biomolecules secreted in the body changes due to excitement or tension.

For example, the brain waves are measured using a brain activity meter, such as an optical, magnetic, or potential type meter, included in the measurement device 1, and there is a property that a waveform changes due to excitement or tension.

For example, the fMRI information is measured by the MRI device included in the measurement device 1, and includes a blood flow rate and distribution of oxygenated hemoglobin in each activity region in the brain. With regard to the fMRI information, there is a property that an activity region in the brain changes due to excitement or tension. For example, excitement or tension related to an emotion appears as a change in a blood flow rate in a limbic system (amygdala), hypothalamus, cerebellum, brainstem, hippocampus, or the like. Such a change in a blood flow rate changes the distribution of oxygenated hemoglobin in the brain.

The output device 2 includes a display such as an organic electro-luminescence (EL) display or a liquid crystal display, a speaker, or the like. The output device 2 receives data indicating feelings and intentions which is created by the intention emergence device 100, displays the received data on the display, or outputs the received data from the speaker as a sound.

Meanwhile, the output device 2 may be provided inside the intention emergence device 100. In addition, the output device 2 may be another robot, another artificial intelligence (that is, another intention emergence device 100), or the like which is connected to a network. In addition, the output device 2 may be a portable communication terminal such as a smartphone, an automobile, or the like.

The intention emergence device 100 illustrated in FIG. 1 includes an acquisition unit 10, a detection unit 20, a decision unit 30, a calculation unit 40, an element unit 50, an emergence unit 60, a control unit 70, and a storage unit 80. Functions of the detection unit 20, the decision unit 30, the calculation unit 40, the emergence unit 60, and the control unit 70 may be realized by an intention emergence program to be executed by the execution processing device of the intention emergence device 100, or may be realized by hardware.

The acquisition unit 10 is an input-output, interface or the like, and acquires data including sound information and physiological information on the subject PA from the measurement device 1. The acquisition unit 10 outputs the acquired data to the detection unit 20.

Meanwhile, the acquisition unit 10 may acquire data including at least the sound information on the subject PA from the measurement device 1, and may acquire character information, such as an instruction command input from the subject PA, through an input device such as a keyboard included in the intention emergence device 100. In addition, the acquisition unit 10 may include a network interface, and may acquire information which the subject PA may be interested in, together with the data of the sound information on the subject PA through a network.

The detection unit 20 detects feelings of the subject PA using the sound information among the pieces of data of the subject PA which are acquired by the measurement device 1. For example, the detection unit 20 defects feelings such as "anger", "sorrow", "normal", and "pleasure" using a feeling table generated using a technique disclosed in Japanese Unexamined Patent Application Publication No. 2009-29464 and stored in the storage unit 80, and the sound information on the subject PA. The detection unit 20 outputs detection results on the feelings of the subject PA to the decision unit 30. In addition, the detection unit 20 stores the detection results on the feelings of the subject PA in the storage unit 80 together with the acquired data.

Meanwhile, in order to generate the feeling table, the intention emergence device 100 makes each of a plurality of persons hear sounds extracted in units of utterance in daily conversation, television drama, and the like in a random order, and makes the person determine which feeling a speaker receives from a sound in each utterance unit. The intention emergence device 100 extracts a sound in an utterance unit having a feeling common to determination results, and calculates values of parameters such as the intensity, fundamental frequency, frequency distribution, and intonation of a sound waveform in each utterance unit.

The intention emergence device 100 calculates information equivalent to feelings and psychological attributes resulting from information on vocabulary and syntax equivalent to feelings and psychological attributes by using means for acquiring language information from sounds such as sound recognition. The intention emergence device 100 analyzes in what value ranges a plurality of parameters in each sound are distributed to show changes with time and what combination of the parameters is used, as the reason sounds are determined to be in respective feeling conditions. The intention emergence device 100 generates conditions of the feelings as the feeling table by listing the values of the parameters and combinations patterns based on analysis results, and stores the generated feeling table in the storage unit 80.

In addition, the detection unit 20 may detect utterance contents uttered by the subject FA from the sound information on the subject PA. That is, when the subject PA utters "kyou wa ii tenki desune" (in Japanese), the detection unit 20 extracts breaks for each phoneme like "kyo/u/wa/i/i/te/n/ki/de/su/ne" (in Japanese). Further, the detection unit 20 breaks for each word from the sound information on the subject PA. For example, when sound information of "kyou wa ii tenki desune" (in Japanese) is input, the detection unit 20 extracts breaks for each word like "kyo/u/wa/i/i/te/n/ki/de/su/ne" (in Japanese).

The detection unit 20 executes recognition and syntax analysts for each word included in a sound of the subject PA, based on information indicating a phoneme and breaks of a word in the extracted sound of the subject PA. That is, the detection unit 20 recognizes information indicating 5W1H of "who", "what", "when", "where", "why", and "how" from a sound of the subject PA, and ascertains contents of the sound of the subject PA as a natural language. In addition, the detection unit 20 may detect conditions or a situation where the subject PA lies, from the sound of the subject PA based on the ascertained contents of the sound. The detection unit 20 stores the detected utterance contents, conditions, and the like of the subject PA in the storage unit 80 together with the feelings of the subject PA.

For example, the decision unit 30 determines weighting coefficients for parameters such as intensity and fundamental frequency obtained from the sound information in accordance with the feelings of the subject PA which is detected by the detection unit 20 and parameters such as blood pressure and body temperature included in the physiological information.

Meanwhile, the feelings of the subject PA which is detected by the detection unit 20 is not so simple as to be classified into any one of feelings, and a plurality of feelings are detected in a mixed form. In addition, the feelings of the subject PA changes according to the conditions or situation where the subject PA lies. For this reason, it is preferable that the decision unit 30 decides weighting coefficients for the sound information and the physiological information on the subject PA in accordance with the feelings of the subject PA, in consideration of the utterance contents, conditions, and the like of the subject PA which are detected by the detection unit 20.

For example, when the detected changes in the feelings of the subject PA with time are consistent with changes with time showing specific changes with time determined in advance, that is, changes with time showing a "strong impression" state, the decision unit 30 decides weighting coefficients for the sound information and the physiological information on the subject PA to be a large value. When a change in the detected feelings is large, the same utterance contents are repeatedly detected at frequent intervals, or the utterance contents are easy to be impressed, the decision unit 30 considers a "strong impression" state and decides weighting coefficients for the sound information and the physiological information on the subject PA to be a large value. In this case, it is preferable that the detected feelings, utterance contents, and the like of the subject PA are held in the storage unit 80 as intense memories of the past in human memory even when time passes.

On the other hand, when changes in the detected feelings of the subject PA with time are not consistent with changes with time determined in advance, that is changes with time showing a "strong impression" state, that is, are changes with time showing a "weak impression" state, the decision unit 30 decides weighting coefficients for the sound information and the physiological information on the subject PA to be a small value. In addition, when a change in the detected feelings is small or utterance contents are detected once or a plurality of times, the decision unit 30 considers a "weak impression" state and decides weighting coefficients for the sound information and the physiological information on the subject PA to be a small value. In this case, the detected feelings and utterance contents of the subject PA are erased from the storage unit 80 with the lapse of time, as vague memories of the past in human memory. Thereby, it is possible to suppress the amount of data stored in the storage unit 80.

Meanwhile, the decision unit 30 may decide weighting coefficients for the sound information and the physiological information on the subject PA using any one of a signal output by the element unit 50 to be described later and feelings of the intention emergence device 100 which is decided by the emergence unit 60, and the detected feelings of the subject PA. Thereby, the personality and individuality of the intention emergence device 100 can be changed based on influence inside the intention emergence device 100 together with influence from the outside such as the subject PA.

The calculation unit 40 calculates energy which involves in human emotions and organ activities with using the data acquired from the measurement device 1 and the coefficients decided by the decision unit 30. The operation of the calculation unit 40 will be described in FIGS. 2 and 3.

The element unit 50 includes a plurality of elements, such as a metamorphose element and spintronics, which changes the state of a material in accordance with an input of the energy calculated by the calculation unit 40. The element unit 50 outputs a signal indicating a change in the state of a material in each of the plurality of elements to the emergence unit 60 and the control unit 70 as homeostasis in each of human emotion and organ activities. The operation of the element unit 50 will be described in FIGS. 2 and 3.

The emergence unit 60 decides feelings and intentions in accordance with a change in the state (homeostasis) of the material included in the signal output from each of the elements of the element unit 50, for example, using an emergence table ET stored in the storage unit 80. The operation and the emergence table ET of the emergence unit 60 will be described in FIG. 4.

The control unit 70 monitors the operation of the plurality of elements included in the element unit 50, and performs phase transition of the state of the material in the plurality of elements when the amount of change in the state of the material in at least one element among the plurality of elements is equal to or less than a predetermined amount. The operation of the control unit 70 will be described in FIG. 3.

The storage unit 80 is a hard disk drive, a memory, or the like, and stores data such as the emergence table ET together with an intention emergence program. In addition, the storage unit 80 stores the data including the sound information and the physiological information on the subject PA which is acquired by the acquisition unit 10, and the feelings, utterance contents, and the like of the subject PA which are detected by the detection unit 20. Meanwhile, the storage unit 80 is disposed inside the intention emergence device 100, but may be disposed outside the intention emergence device 100. In this case, it is preferable that the storage unit 80 is connected to the intention emergence device 100 through a network or the like.

Meanwhile, the intention emergence program can be recorded in a removable disc, such as a compact disc (CD) or a digital versatile disc (DVD), and distributed. In addition, the intention emergence device 100 may download the intention emergence program form a network through a network interface included in the intention emergence device 100, and may store the downloaded program in the storage unit 80.

Figure 2:
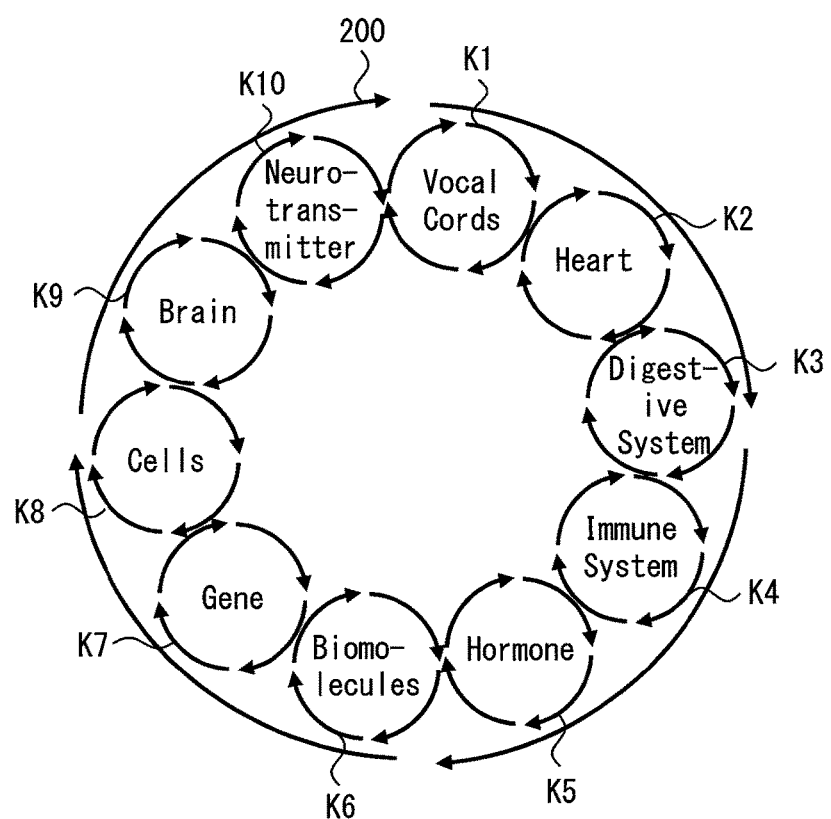
FIG. 2 is a schematic diagram illustrating an example of a chain of homeostasis in a human being.

FIG. 2 is a schematic diagram illustrating an example of a chain of homeostasis in a human being. In FIG. 2, for example, a circulation system 200 is configured by representing a balance of homeostasis of the entire human body by the rotation of a circular figure. The circulation system 200 further includes, for example, a plurality of circulation systems K (K1 to K10) such as materials and organs forming a human being. In FIG. 2, the circulation systems K1 to K10 are represented by the rotation of circles that are linked together to maintain a balance of homeostasis and are smaller than the circulation system 200. For example, the circulation system K1 indicates the homeostasis of human emotions based on a sound uttered by the human being through the vocal cords. For example, the circulation system K2 indicates the homeostasis of the heart of the human being based on a heart rate, a heart rate fluctuation, and the like. For example, the circulation system K3 indicates the homeostasis of the digestive system of the human being such as the stomach, the small intestine, or the large intestine. For example, the circulation system K4 indicates the homeostasis of the immune system that protects the human being from illness or the like. For example, the circulation system K5 indicates the homeostasis of hormone that transmits information for adjusting the movement of an organ included in the living body of the human being.

In addition, for example, the circulation system K6 indicates the homeostasis of biomolecules such as a plurality of types of protein generated by a gene of the human being. For example, the circulation system K7 indicates the homeostasis of a gene of the human being. For example, the circulation system K8 indicates the homeostasis of activity of cells forming the human being. For example, the circulation system K9 indicates the homeostasis of activity of the limbic system of the human being which includes amygdala and the like in the brain which is closely related to an emotion. For example, the circulation system K10 indicates the homeostasis of a neurotransmitter that mediates the transmission of information at synapses.

The intention emergence device 100 illustrated in FIG. 1 obtains homeostasis in the circulation system 200 of the intention emergence device 100 using the element unit 50, in order to operate as artificial intelligence.

Meanwhile, the circulation system 200 is configured to include ten circulation systems K1 to K10, but may include any number of plurality of circulation systems other than ten. In addition, each of the circulation systems K may further include a plurality of circulation systems. For example, the circulation system K1 of the vocal cords may include a plurality of circulation systems indicating emotions such as anger, normal, sorrow, and pleasure of a human being. In addition, for example, the circulation system K2 of the heart may include a plurality of circulation systems indicating a heart rate, a heart rate fluctuation, and the like of a human being.

In addition, the circulation system 200 indicates homeostasis in the entire human body, but may indicate homeostasis in one part such as a human brain or may indicate homeostasis in human society such as a company or a nation. For example, when the circulation system 200 indicates homeostasis in a human brain, each circulation system K indicates homeostasis in each nerve cell of the brain. In addition, when the circulation system 200 indicates homeostasis in human society, each circulation system K indicates homeostasis in individual human beings.

In addition, the chain of homeostasis in human beings has been shown like the circulation system 200 illustrated in FIG. 2, but is not limited thereto and may be shown in other forms.

FIG. 3 illustrates an example of the element unit 50 illustrated in FIG. 1. The element unit 50 includes N elements 51 (51(1) to 51(N)) and a supply unit 52.

For example, the element 51 is a metamorphose element including a material such as a metal oxide or a polymeric hydrogel that changes (phase transition) between a solid and a liquid according to a voltage, a temperature, and the like which are input from the outside. The element 51 such as a metamorphose element outputs a signal indicating a change in the state of the material to the emergence unit 60 and the control unit 70. Meanwhile, since the state of the material continuously changes between a solid and a liquid in the element 51, it is possible to output a signal having a value continuously changing in accordance with the change in the state of the material. Since homeostasis in each circulation system K also changes continuously, a value indicating the change in the state of the material in the signal output by the element 51 can be used as the homeostasis in each circulation system K. The intention emergence device 100 reproduces a reaction such as a double-loop in a human brain determination process by using the N elements 51.

Consequently, the intention emergence device 100 illustrated in FIG. 1 sets each element 51 to be each circulation system K (for example, N=10) illustrated in FIG. 2, and uses the signal indicating the change in the state of the material output by the element 51 as the homeostasis in each circulation system K. Meanwhile, since the circulation systems K have an influence on each other, and thus the elements 51 are connected to each other so as to be capable of transmitting and receiving the signal indicating the change in the state of the material to and from each other.

The supply unit 52 is, for example, a power supply, a light source, a heat source, a sprayer, or the like. For example, when the supply unit 52 is a power supply, the supply unit supplies a voltage, a current, or the like according to the energy calculated by the calculation unit 40 to the N elements 51. In addition, when the supply unit 52 is a light source, the supply unit irradiates the N elements 51 with electromagnetic waves having intensity and frequency according to the energy calculated by the calculation unit 40. In addition, when the supply unit 52 is a heat source, the supply unit supplies thermal energy according to the energy calculated by the calculation unit 40 to the N elements 51. When the supply unit is a sprayer, the supply unit sprays a solvent having concentration and temperature according to the energy calculated by the calculation unit 40.

The calculation unit 40 calculates energy TE which involves in emotions and organ activities when the intention emergence device 100 operates as artificial intelligence, for example, using the data acquired by the acquisition unit 10, the coefficients decided by the decision unit 30, and Expression (1).

$$TE = \sum_{i=1}^{M} w_i \cdot a_i \tag{1}$$

Meanwhile, $a_i$ denotes the value of a parameter such as intensity or fundamental frequency in the sound information obtained by the detection unit 20, and the value of a parameter such as blood pressure included in the physiological information measured by the measurement device 1. In addition, $w_i$ denotes weighting coefficients for the value $a_i$ of each parameter. In addition, M denotes the number of parameters.

Meanwhile, the calculation unit 40 has calculated the energy TE using Expression (1), but may calculate the energy TE using a function F ($a_i$, $w_i$). It is preferable that the function F ($a_i$, $w_i$) is appropriately decided in accordance with personality and individuality desired to be added to the intention emergence device 100.

In addition, the energy TE calculated by the calculation unit 40 may be set to a negative value. In this case, for example, the supply unit 52 may apply a negative voltage to the element 51, and may cool the element 51.

Meanwhile, the element 51 changes the state of a material by the energy TE supplied through the supply unit 52, but the state of the material may converge to a predetermined state with the lapse of time. In this case, the amount of change in the state of the material in the element 51 is decreased (that is, homeostasis in the circulation system K is deteriorated).

In order to avoid this, the control unit 70 monitors the change (homeostasis) in the state of the material in each element 51, based on a signal output from each element 51. When the amount of change in the state of the material of at least one element 51 among the N elements 51 is set to be equal to or less than a predetermined amount for a predetermined period of time or more, the control unit 70 determines that homeostasis is deteriorated. The control unit 70 outputs an instruction for performing phase transition of the state of the material, for example, from a solid portion to a liquid or from a liquid portion to a solid, to all of the elements 51. Thereby, the intention emergence device 100 can avoid the deterioration of homeostasis.

In addition, an operation in which the control unit 70 gives an instruction for performing phase transition to the N elements 51 is equivalent to the change of mood such as a rest or a walk, for example, when work, discussions, and the like have come to a standstill in a case of a human being (a reaction such as a double-loop in a human brain determination process is repeatedly executed). By changing the mood, the human being may converge reactions such as a double-loop in the brain and conceive thinking and ideas of new viewpoints. Consequently, the control unit 70 gives an instruction for performing phase transition to the N elements 51, and outputs a signal indicating a change in the state of the material different from that before the phase transition to the elements 51. The emergence unit 60 decides feelings and intentions different from those before the phase transition, based on the change in the state of the material different from that before the phase transition which is included in the signal of each of the elements 51. That is, the intention emergence device 100 sets the instruction for performing phase transition given by the control unit 70 to be a timing for converging reactions such as a double-loop in the intention emergence device 100, and decides new feelings and intentions different from those before the phase transition. Thereby, the intention emergence device 100 can decide various intentions, determinations, and the like according to its own mood, conditions, scenes, and the like.

Meanwhile, it is preferable that the predetermined amount and the predetermined period of time are appropriately set in accordance with personality and individuality desired to be added to the intention emergence device 100. In addition, the predetermined amount, and the predetermined period of time may be set to values different for each element 51.

In addition, it is preferable to appropriately set the number of elements 51 in which the amount of change in the state of the material when the control unit 70 outputs an instruction for performing phase transition is set to be equal to or less than the predetermined amount, in accordance with personality and individuality desired to be added to the intention emergence device 100. For example, as the number of elements 51 decreases, the intention emergence device 100 can react to data input from the subject PA in a shorter period of time. On the other hand, the intention emergence device 100 reacts to the data input from the subject PA more slowly as the number of elements 51 increases, but can show a more appropriate reaction to the subject PA.

In addition, the control unit 70 may output an instruction for performing phase transition to all of the elements 51 when the state of the material in at least, one element 51 among the N elements 51 is a predetermined state. Meanwhile, it is preferable that the predetermined state is appropriately set in accordance with personality and individuality desired to be added to the intention emergence device 100. In addition, the predetermined state may be set differently for each element 51.

FIG. 4 illustrates an example of the emergence table ET illustrated in FIG. 1. The emergence table ET includes storage regions for feelings and intentions and storage regions for the elements 51(1) to 51(N).

In the storage regions for feelings and intentions, combinations of feelings and intentions such as "anger, suppress", "anger, retort", "normal, converse", and "normal, agree" are stored.

In each of the storage regions for the elements 51(1) to 51(N), a combination of changes (homeostasis) in the state of the material indicated by a signal output by each element 51 for the emergence unit 60 to decide feelings and intentions stored in the storage regions for feelings and intentions is stored. Meanwhile, a storage region having "–" stored therein indicates that the storage, region is not included in conditions of feelings and intentions decided by the emergence unit 60.

Regarding a change in the stare of the material which is stored in the storage region for each element 51, a change in the state indicated by the material of the element 51 for a predetermined period of time is set in advance based on results of simulation, for example, by executing the simulation disclosed in Patent Document 1. Meanwhile, it is preferable that a change in the state of the material which is stored in the storage region for each element 51 is appropriately set in accordance with personality and individuality desired to be added to the intention emergence device 100.

In addition, a change in the state of the material which is stored in the storage region for each of the elements 51(1) to 51(N) may be changed in accordance with the weighting coefficients decided by the decision unit 30, the feelings and the intentions decided by the emergence unit 60, and the like. In addition, the order of changes in the states of the materials stored in the storage regions for the elements 51(1) to 51(N) may be changed in accordance with the weighting coefficients decided by the decision unit 30, the feelings and the intentions decided by the emergence unit 60, and the like. Thereby, the personality and individuality of the intention emergence device 100 can be changed based on a change inside the intention emergence device 100 together with influence from the outside such as the subject PA.

The emergence unit 60 decides feelings and intentions based on the emergence table ET stored in the storage unit 80 and the change in the state of the material included in the signal output from each of the N elements 51. The emergence unit 60 outputs results of the decided feelings and intentions to the output device 2. For example, when the storage unit 80 stores an utterance table storing sound data, which is uttered by the intention emergence device 100 in accordance with the utterance contents of the subject PA detected by the detection unit 20 and the decided feelings, and intentions and character data, the emergence unit 60 extracts the sound data corresponding to the detected utterance contents of the subject PA and the decided feelings and intentions, and the like from the utterance table. The intention emergence device 100 outputs the extracted sound data from the speaker included in the output device 2. Thereby, the intention emergence device 100 can have a conversation with the subject PA.

In addition, the intention emergence device 100 outputs the feelings and intentions received through the utterance of the subject PA and an impression of the subject PA to the output device 2 based on the results of the feelings and intentions decided by the emergence unit 60. The intention emergence device 100 may output a communication advice or the like for the subject PA to the output device 2 so that the subject PA can grasp atmosphere of the place and perform communication. Thereby, it is possible to improve a communication ability of the subject PA.

In addition, when the subject PA suffers from a psychiatric disorder or the like, the intention emergence device 100 may output an advice on the psychiatric disorder or the like for the subject PA, or the like to the output device 2 in accordance with the results of the feelings and intentions decided by the emergence unit 60. Thereby, the intention emergence device 100 can achieve an improvement in a medical condition of the subject PA.

FIG. 5 illustrates an example of an intention emergence process in the intention emergence device 100 illustrated in FIG. 1. The processing illustrated in FIG. 5 is realized by executing an intention emergence program stored in the storage unit 80 by the execution processing device of the intention emergence device 100. That is, the processing illustrated in FIG. 5 indicates an embodiment of an intention emergence program and an intention emergence method. Meanwhile, the processing illustrated in FIG. 5 may be realized by hardware mounted on the intention emergence device 100. In this case, the detection unit 20, the decision unit 30, the calculation unit 40, the emergence unit 60, and the control unit 70 illustrated in FIG. 1 are realized by circuits disposed inside the intention emergence device 100.

In step S100, the acquisition unit 10 acquires data including the sound information and the physiological information on the subject PA which are measured by the measurement device 1. The acquisition unit 10 outputs the acquired data to the detection unit 20.

Next, in step S110, the detection unit 20 detects a feeling such as "anger" or "normal" in the subject PA using the sound information on the subject PA in the data acquired in step S100. The detection unit 20 outputs a detection result on the feeling of the subject PA to the decision unit 30.

Next, in step S120, the decision unit 30 decides weighting coefficients for the sound information and the physiological information on the subject PA in accordance with the feelings of the subject PA which is detected in step S120.

Next, in step S130, the calculation unit 40 calculates energy TE which involves in human emotions and organ activities, with the data acquired in step S100, the coefficients decided in step S120, and Expression (1).

Next, in step S140, the element unit 50 supplies the energy TE calculated in step S130 to the N elements 51 through the supply unit 52. Each of the elements 51 changes the state of the material in accordance with the supplied energy TE, and outputs a signal indicating a change in the state of the material to each of the emergence unit 60 and the control unit 70 as homeostasis in each circulation system K.

Next, in step S150, the control unit 70 receives the signal output from each of the elements 51 in step S140, and monitors a change (homeostasis) in the state of the material in each of the element 51. The control unit 70 determines whether or not the amount of change in the stare of the material in at least one element 51 among the N elements 51 is equal to or less than a predetermined amount. When the amount of change in the state of the material of the element 51 is equal to or less than the predetermined amount for a predetermined period of time or more, the processing of the intention emergence device 100 proceeds to step S160. On the other hand, when the amount of change in the state of the material of the element 51 is not equal to or less than the predetermined amount for the predetermined period of time, the processing of the intention emergence device 100 proceeds to step S170.

In step S160, the control unit 70 outputs an instruction for performing phase transition of the state of the material to all of the elements 51. The processing of the intention emergence device 100 proceeds to step S170.

In step S170, the emergence unit 60 decides feelings and intentions based on the emergence table ET stored in the storage unit 80 and the change in the state of the material included in the signal output from each of the N elements 51. Alternatively, the emergence unit 60 decides feelings and intentions based on the change in the state of the material included in the signal output from each of the elements 51 and the emergence table ET, after the phase transition is performed in step S160. The emergence unit 60 outputs results of the decided feelings and intentions to the output device 2. For example, when an utterance table storing sound data, which is uttered by the intention emergence device 100 in accordance with the utterance contents of the subject PA which are detected by the detection unit 20 and the decided feelings and intentions, and character data is stored in the storage unit 80, the emergence unit 60 extracts the sound data corresponding to the detected utterance contents of the subject PA and the decided feelings and intentions, and the like from the utterance table. The intention emergence device 100 outputs the extracted sound data from the speaker included in the output device 2, and has a conversation with the subject PA.

In addition, the intention emergence device 100 may output the feelings and intentions received through the utterance of the subject PA and an impression of the subject PA to the output device 2 based on the results of the feelings and intentions decided by the emergence unit 60. The intention emergence device 100 outputs a communication advice or the like for the subject PA to the output device 2 so that the subject PA can grasp atmosphere of the place and perform communication, to thereby achieve an improvement in a communication ability of the subject PA.

In addition, when the subject PA suffers from a psychiatric disorder or the like, the intention emergence device 100 outputs an advise on the psychiatric disorder or the like for the subject PA, or the like to the output device 2 in accordance with the results of the feelings and intentions decided by the emergence unit 60, to thereby achieve an improvement in a medical condition of the subject PA.

The intention emergence device 100 terminates the intention emergence process. The intention emergence device 100 repeatedly executes the processes of steps S100 to S170 whenever receiving the data of the subject PA from the measurement device 1.

Meanwhile, in the processing illustrated in FIG. 5, the processes of steps S100 to S140 and the processes of steps S150 to S170 may be executed in parallel.

As described above, in the embodiment illustrated in FIG. 1 to FIG. 5, the decision unit 30 decides weighting coefficients for the sound information and the physiological information included in the data acquired by the acquisition unit 10, in accordance with the feelings of the subject PA which is detected from the sound information on the subject PA by the detection unit 20. The element unit 50 inputs the energy TE calculated by the calculation unit 40 using the weighting coefficients decided by the decision unit 30 to the N elements 51 through the supply unit 52. Each of the elements 51 outputs a signal including a change in the state of the material to the emergence unit 60 and the control unit 70 as homeostasis in each of human emotions and organs. The emergence unit 60 decides feelings and intentions in accordance with a change in the state, of the material indicated by the signal output from each of the elements 51, and the control unit 70 outputs an instruction for performing phase transition to the N elements 51 and performs phase, transition of the state of the material when the amount of change in the state of the material in at least one element 51 among the N elements 51 is equal to or less than a predetermined amount.

That is, the intention emergence device 100 sets the instruction for performing phase transition given by the control unit 70 to be a timing for converging reactions such as a double-loop in the intention emergence device 100, and decides new feelings and intentions different from those before the phase transition. Thereby, the intention emergence device 100 can decide various intentions, determinations, and the like according to its own mood, conditions, scenes, and the like.

In addition, the subject PA may be another intention emergence device 100 instead of a human being. In this case, data acquired by the intention emergence device 100 from another intention emergence device 100 may be only sound information output by the other intention emergence device 100, or a signal output by each element 51 of the other intention emergence device 100 may be used as physiological information. Thereby, the intention emergence device 100 can simulate the development of communication in a human being.

Meanwhile, the intention emergence device 100 illustrated in FIG. 1 may be applied to psychological counseling such as psychoanalysis, behavior prediction, or behavior analysis and an interview or prescription in psychiatric care or general medical care. For example, the intention emergence device 100 may be applied to a robot, artificial intelligence, a vehicle, a call center, entertainment the internet, a portable terminal device application or service of a smart phone, a tablet type terminal, or the like, and a retrieval system. In addition, the intention emergence device 100 may be applied to a diagnostic device, an automatic inquiry device, a disaster triage, and the like. In addition, the intention emergence device 100 may be applied to a financial credit management system, behavior prediction, a company, a school, a government agency, a police, the military, information analysis in information collection activity or the like, psychological analysis leading to lie detection, and organization group management. In addition, the intention emergence device 100 may be applied to a system for managing the health of the mind and behavior prediction of a member, a researcher, an employee, a manager of an organization, or the like, a system for controlling environment such as a house, an office, an airplane, or a spacecraft, or means for knowing the state of the mind or behavior prediction of a family member or a friend. In addition, the intention emergence device 100 may be applied to music, movie distribution, general information retrieval, information analysis management, information processing, or customer sensibility preference market analysis, a system that manages these through a network or on a stand-alone basis, and the like.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to exact construction and operation illustrated and described, and accordingly all suitable modifications and equivalents may be resorted to, falling within the scope thereof.

REFERENCE SIGNS LIST

1 MEASUREMENT DEVICE
2 OUTPUT DEVICE
10 ACQUISITION UNIT
20 DETECTION UNIT
30 DECISION UNIT
40 CALCULATION UNIT
50 ELEMENT UNIT
51(1) TO 51(N) ELEMENT
52 SUPPLY UNIT
60 EMERGENCE UNIT
70 CONTROL UNIT
80 STORAGE UNIT
100 INTENTION EMERGENCE DEVICE
200, K1 TO K10 CIRCULATION SYSTEM
ET EMERGENCE TABLE

The invention claimed is:

1. An intention emergence device comprising:
an acquisition unit acquiring data including at least sound information uttered by a subject;
a detection unit detecting feelings of the subject using the data being acquired;
a decision unit deciding weighting coefficients for the data acquired in accordance with the feelings of the subject being detected;
a calculation unit calculating energy which involves in human emotions and organ activities with the data and the coefficients;
a plurality of elements, each of which has a material changing a state in accordance with input of the energy calculated by the calculation unit, outputting signals each of which indicates the change in the state of the material as homeostasis in each of the human emotions and the organ activities;
an emergence unit deciding feelings and intentions in accordance with the change in the state of the material included in the signals output from each of the plurality of elements; and
a control unit performing phase transition of the state of the material in each of the plurality of elements when an amount of change in the state of the material in at least one element among the plurality of elements is equal to or less than a predetermined amount or when the state of the material in at least one element among the plurality of elements is in a predetermined state.

2. The intention emergence device according to claim 1, wherein
the plurality of elements are mutually connected to each other so as to be capable of transmitting and receiving the signals.

3. The intention emergence device according to claim 1, wherein
the decision unit decides the weighting coefficients for the data in accordance with the feelings being detected and the feelings decided by the emergence unit.

4. An intention emergence method comprising:
acquiring data including at least sound information uttered by a subject;
detecting feelings of the subject using the data being acquired;
deciding weighting coefficients for the data acquired in accordance with the feelings being detected;
calculating energy which involves in human emotions and organ activities with the data and the coefficients;
inputting the energy being calculated to each of a plurality of elements which has a material changing a state in accordance with the input, and outputting, from each of the plurality of elements, signals each of which indicates the change in the state of the material as homeostasis in each of the human emotions and the organ activities;

deciding feelings and intentions in accordance with the change in the state of the material included in the signals output from each of the plurality of elements; and performing phase transition of the state of the material in each of the plurality of elements when an amount of change in the state of the material in at least one element among the plurality of elements is equal to or less than a predetermined amount or when the state of the material in at least one element among the plurality of elements is in a predetermined state.

5. A non-transitory computer-readable recording medium that stores an intention emergence program that causes a computer to execute a process comprising:

acquiring data including at least sound information uttered by a subject;

detecting feelings of the subject using the data being acquired;

deciding weighting coefficients for the data acquired in accordance with the feelings being detected;

calculating energy which involves in human emotions and organ activities with the data and the coefficients;

inputting the energy being calculated to each of a plurality of elements which has a material changing a state in accordance with the input, and outputting, from each of the plurality of elements, signals each of which indicates the change in the state of the material as homeostasis in each of the human emotions and the organ activities;

deciding feelings and intentions in accordance with the change in the state of the material included in the signals output from each of the plurality of elements; and performing phase transition of the state of the material in each of the plurality of elements when an amount of change in the state of the material in at least one element among the plurality of elements is equal to or less than a predetermined amount or when the state of the material in at least one element among the plurality of elements is in a predetermined state.

* * * * *